US00PP26914P2

(12) United States Plant Patent
Warner

(10) Patent No.: US PP26,914 P2
(45) Date of Patent: Jul. 12, 2016

(54) ROSE PLANT NAMED 'CHEWHOCAN'

(50) Latin Name: *Rosa hybrida*
Varietal Denomination: Chewhocan

(71) Applicant: Christopher H. Warner, Newport (GB)

(72) Inventor: Christopher H. Warner, Newport (GB)

(73) Assignee: Spring Meadow Nursery, Inc., Grand Haven, MI (US)

( * ) Notice: Subject to any disclaimer, the term of this patent is extended or adjusted under 35 U.S.C. 154(b) by 56 days.

(21) Appl. No.: 13/998,221

(22) Filed: Oct. 11, 2013

(51) Int. Cl.
*A01H 5/02* (2006.01)

(52) U.S. Cl.
USPC ..... Plt./104

(58) Field of Classification Search
USPC ..... Plt./104
See application file for complete search history.

(56) References Cited

PUBLICATIONS

Help Me Find (retrieved from internet on Mar. 25, 2015).*

* cited by examiner

*Primary Examiner* — Keith Robinson
(74) *Attorney, Agent, or Firm* — C. A. Whealy

(57) ABSTRACT

A new and distinct cultivar of Rose plant named 'Chewhocan', characterized by its upright, outwardly spreading and mounding plant habit; glossy green-colored leaves; freely branching growth habit; freely flowering habit; clear yellow-colored flowers that resist fading; resistance to Black Spot; and good garden performance.

2 Drawing Sheets

Botanical designation: *Rosa hybrida.*
Cultivar denomination: 'CHEWHOCAN'.

BACKGROUND OF THE INVENTION

The present Invention relates to a new and distinct Rose plant, botanically known as *Rosa hybrida*, commercially used as an ornamental Shrub Rose and hereinafter referred to by the name 'Chewhocan'.

The new Rose plant is a product of a planned breeding program conducted by the Inventor in Newport, Shropshire, United Kingdom. The objective of the breeding program was to develop new uniform and disease-resistant shrub Rose plants with large and attractive flowers.

The new Rose plant originated from a cross-pollination made by the Inventor in June, 2000 of *Rosa hybrida* 'Horcoherent', disclosed in U.S. Plant Pat. No. 15,982, as the female, or seed, parent with *Rosa hybrida* 'Chewpatel', not patented, as the male, or pollen, parent. The new Rose plant was discovered and selected by the Inventor in 2005 as a single flowering plant within the progeny of the stated cross-pollination in a controlled environment in Newport, Shropshire, United Kingdom.

Asexual reproduction of the new Rose plant by softwood cuttings at Newport, Shropshire, United Kingdom since 2005 has shown that the unique features of this new Rose plant are stable and reproduced true to type in successive generations of asexual reproduction.

SUMMARY OF THE INVENTION

The following traits have been repeatedly observed and are determined to be the unique characteristics of 'Chewhocan'. These characteristics in combination distinguish 'Chewhocan' as a new and distinct Rose plant:

1. Upright, outwardly spreading and mounding plant habit.
2. Glossy green-colored leaves.

3. Freely branching growth habit.
4. Freely flowering habit.
5. Clear yellow-colored flowers that resist fading.
6. Resistant to Black Spot (*Diplocarpon rosae*).
7. Good garden performance.

Plants of the new Rose differ primarily from plants of the female parent, 'Horcoherent', in flower color as plants of 'Horcoherent' have orange, pink and yellow-colored flowers.

Plants of the new Rose differ from plants of the male parent, 'Chewpatel', in the following characteristics:

1. Plants of the new Rose are more mounding than and not as spreading as plants of 'Chewpatel'.
2. Flowers of plants of the new Rose are not as fragrant as flowers of plants of 'Chewpatel'.
3. Plants of the new Rose and 'Chewpatel' differ in flower color as plants of 'Chewpatel' have soft yellow and white-colored flowers.

Plants of the new Rose can be compared to plants of the *Rosa hybrida* 'Chewallbell', disclosed in U.S. Plant patent application Ser. No. 13/998,231. Plants of the new Rose differ primarily from plants of 'Chewallbell' flower color as plants of 'Chewallbell' have clear salmon pink-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph on the first sheet comprises a side perspective view of a typical plant of 'Chewhocan' in a container.

The photograph on the second sheet is a close-up view of a typical open flower of 'Chewhocan'.

DETAILED BOTANICAL DESCRIPTION

Plants of the new Rose have not been observed under all possible environmental conditions and cultural practices. The phenotype may vary somewhat with variations in environmental conditions such as temperature and light intensity, without, however, any variance in genotype. The aforementioned photographs, following observations and measurements describe plants grown in two-gallon containers during the summer in an outdoor nursery in Grand Haven, Mich. and under cultural practices typical of commercial Rose production. Plants were two years old when the photographs and description were taken. In the following description, color references are made to The Royal Horticultural Society Colour Chart, 1995 Edition, except where general terms of ordinary dictionary significance are used.

Botanical classification: *Rosa hybrida* 'Chewhocan'.

Parentage:

*Female, or seed, parent.*—*Rosa hybrida* 'Horcoherent', disclosed in U.S. Plant Pat. No. 15,982.

*Male, or pollen, parent.*—*Rosa hybrida* 'Chewpatel', not patented.

Propagation:

*Type*.—By softwood cuttings.

*Time to initiate roots*.—About 12 days at 25° C.

*Time to produce a rooted young plant*.—About three months at 25° C.

*Root description*.—Somewhat fibrous, fine to thick; white, close to 155A, to brown, close to 200B in color.

*Rooting habit*.—Freely branching; dense.

Plant description:

*Plant form*.—Upright, outwardly spreading and mounding perennial Shrub Rose.

*Growth habit*.—Vigorous growth habit; rapid growth rate.

*Branching habit*.—Freely branching habit; about eleven primary lateral branches develop per plant; dense and bushy growth habit; pinching enhances lateral branch development.

*Plant height*.—About 31 cm.

*Plant width* (*spread*).—About 45 cm.

*Lateral branches*.—Length: About 23 cm. Diameter: About 2 mm. Internode length: About 2.8 cm. Strength: Strong. Texture: Smooth, glabrous. Color: Close to 144B. Thorns: Density: About two to six thorns per node on a developed lateral branch. Shape: Triangular with sharp acuminate apices. Height: About 3 mm to 6 mm. Diameter, at base: About 3 mm to 6 mm. Color: Close to 144D.

Leaf description:

*Arrangement*.—Alternate; pinnately compound with about five leaflets per leaf.

*Leaflet length*.—About 2.6 cm.

*Leaflet width*.—About 1.5 cm.

*Leaflet shape*.—Ovate.

*Leaflet apex*.—Acuminate.

*Leaflet base*.—Obtuse.

*Leaflet margin*.—Serrate.

*Leaflet texture, upper and lower surfaces*.—Smooth, glabrous.

*Leaflet luster, upper and lower surfaces*.—Glossy.

*Leaflet venation pattern*.—Pinnate.

*Leaflet color*.—Developing leaflets, upper surface: Close to 143B. Developing leaflets, lower surface: Close to 144B. Fully expanded leaflets, upper surface: Close to 137B; venation, close to 146C. Fully expanded leaflets, lower surface: Close to 144A; venation, close to 145B.

*Leaf petiole*.—Length: About 8 mm. Diameter: About 1 mm. Texture, upper and lower surfaces: Smooth, glabrous. Color, upper surface: Close to 60B. Color, lower surface: Close to 145A.

Flower description:

*Flower type and habit*.—Rotate rounded flowers arranged singly; flowers face mostly upright or outwardly; freely flowering with plants developing about 44 flowers during the flowering period.

*Natural flowering season*.—Plants flower continuously in the landscape during the summer in Grand Haven, Mich.; during this period flowering is continuous; flowers persistent.

*Fragrance*.—Slightly fragrant; sweet, pleasant.

*Flower buds*.—Height: About 1.5 cm. Diameter: About 1 cm. Shape: Ovoid. Texture: Rugose, glabrous. Color: Close to 6C.

*Flower diameter*.—About 5 cm.

*Flower depth*.—About 1.5 cm.

*Petals*.—Quantity per flower: About 10 to 18 in two to three whorls. Length: About 2 cm. Width: About 1.7 cm. Shape: Obovate. Apex: Obtuse. Base: Attenuate. Margin: Entire. Texture, upper and lower surfaces: Smooth, glabrous. Aspect: Initially upright becoming mostly flat, margins reflexing with development; moderately to weakly undulate. Color: Developing petals, upper surface: Close to 5B. Developing petals, lower surface: Close to 6C. Fully expanded petals, upper surface: Close to 7C; color resists fading but eventually becoming closer to 6D with development; no basal spot observed. Fully expanded petals, lower surface: Close to 6B.

*Sepals*.—Quantity per flower: Four to five. Length: About 1.7 cm. Width: About 6 mm. Shape: Lanceolate. Apex: Aristate. Base: Obtuse. Margin: Entire. Texture, upper and lower surfaces: Smooth, glabrous. Color: Developing sepals, upper surface: Close to 145B. Developing sepals, lower surface: Close to 145A. Fully expanded sepals, upper surface: Close to 145A. Fully expanded sepals, lower surface: Close to 144C.

*Peduncles*.—Length: About 3 cm. Diameter: About 1 mm. Orientation: Erect to about 40° to 50° from vertical. Strength: Strong. Color: Close to 144B.

*Reproductive organs*.—Stamens: Quantity per flower: Numerous, about 63. Anther shape: Oblong. Anther length: About 3 mm. Anther color: Close to 26B. Pollen amount: Moderate. Pollen color: Close to 4D. Pistils: Quantity per flower: About 20. Pistil length: About 1 cm. Stigma shape: Round. Stigma color: Close to 9C. Style length: About 5 mm. Style color: Close to 9C. Ovary color: Close to 144B.

*Fruits*.—Diameter: About 1 cm to 1.2 cm. Shape: Globular. Color: Close to 144A; with frost, color becoming closer to 200A.

*Seeds*.—Diameter: About 4 mm to 5 mm. Shape: Roughly tear-shaped. Color: Close to 160B.

Pathogen & pest resistance: Plants of the new Rose have been observed to be resistant to Black Spot (*Diplocarpon rosae*).

Plants of the new Rose have not been observed to be resistant to pests and other pathogens common to Rose plants.

Garden performance: Plants of the new Rose have been observed have good garden performance and to tolerate rain, wind and temperatures ranging from about −25° C. to about 30° C.

It is claimed:

1. A new and distinct Rose plant named 'Chewhocan' as illustrated and described.

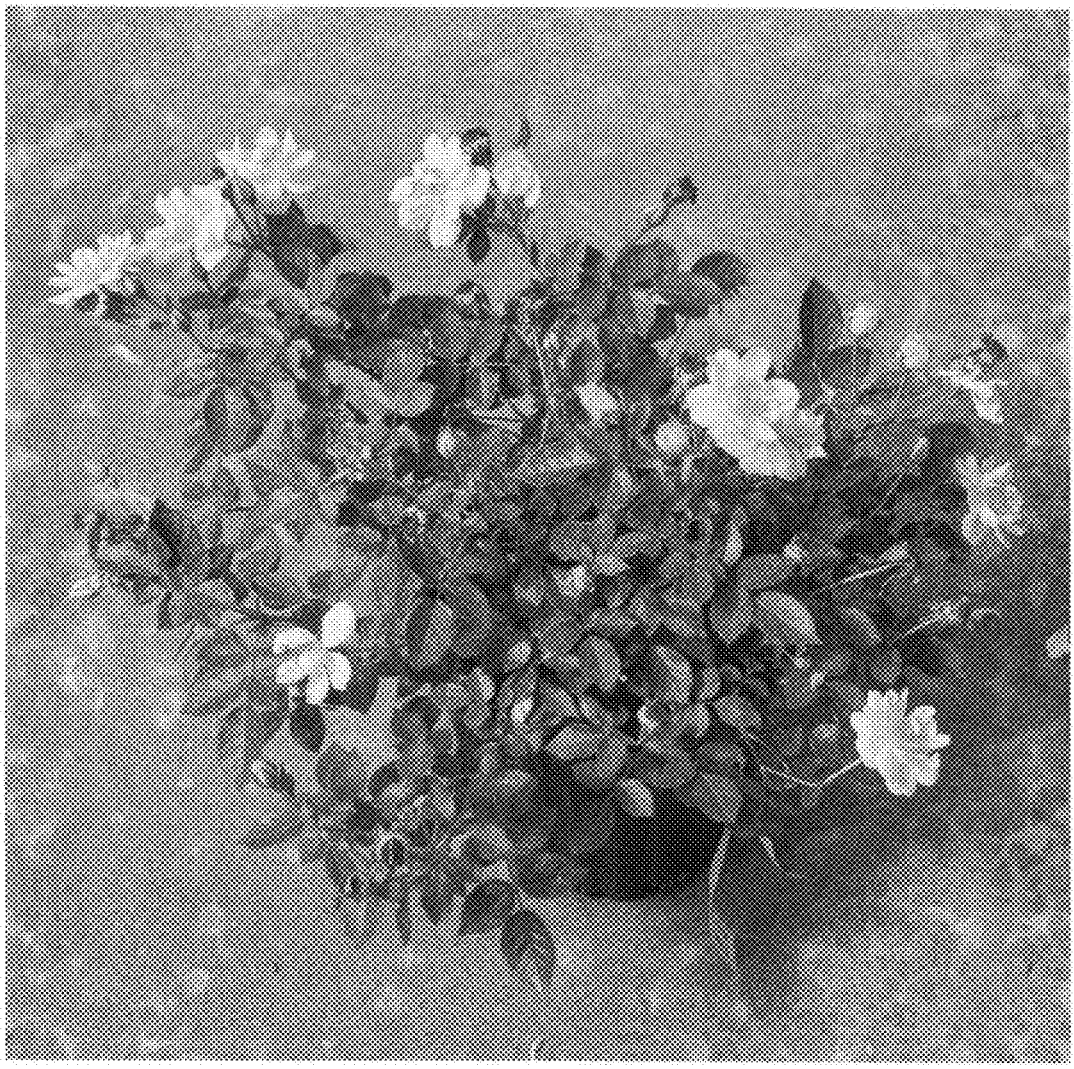

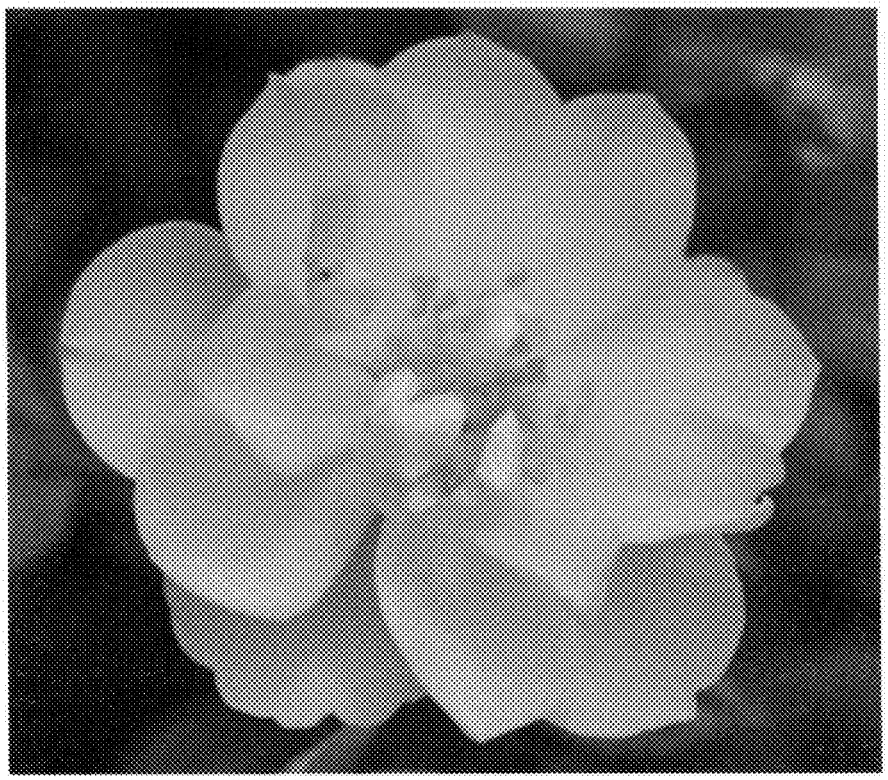

* * * * *